US007004282B2

(12) United States Patent
Manna et al.

(10) Patent No.: US 7,004,282 B2
(45) Date of Patent: Feb. 28, 2006

(54) ULTRASONIC HORN

(75) Inventors: Ronald R. Manna, Valley Stream, NY (US); Dan Voic, Clifton, NJ (US)

(73) Assignee: Misonix, Incorporated, Farmingdale, NY (US)

( * ) Notice: Subject to any disclaimer, the term of this patent is extended or adjusted under 35 U.S.C. 154(b) by 0 days.

(21) Appl. No.: 10/282,150

(22) Filed: Oct. 28, 2002

(65) Prior Publication Data
US 2004/0079580 A1    Apr. 29, 2004

(51) Int. Cl.
*G10K 11/02* (2006.01)
*B06B 1/00* (2006.01)

(52) U.S. Cl. .................. 181/142; 422/128; 204/157.62
(58) Field of Classification Search ............. 181/142.5; 228/1.1, 110.1, 262; 239/102.2, 102.1; 422/128; 204/157.62; 73/662, 663
See application file for complete search history.

(56) References Cited

U.S. PATENT DOCUMENTS

| | | | | |
|---|---|---|---|---|
| 3,937,236 A | | 2/1976 | Runnells ...................... 134/184 |
| 4,872,353 A | * | 10/1989 | Orr et al. .................. 73/864.85 |
| 4,874,137 A | | 10/1989 | Chiba .......................... 241/301 |
| 4,930,532 A | | 6/1990 | Mayer .......................... 134/184 |
| 5,095,188 A | * | 3/1992 | Klein .................... 219/121.14 |
| 5,167,231 A | * | 12/1992 | Matsui ........................ 600/459 |
| 5,171,387 A | * | 12/1992 | Wuchinich ................. 156/73.3 |
| 5,185,728 A | | 2/1993 | Gilchrist ..................... 367/163 |
| 5,459,699 A | | 10/1995 | Walter ......................... 367/142 |
| 5,512,335 A | * | 4/1996 | Miller et al. ................. 427/600 |
| 5,779,985 A | | 7/1998 | Sucholeiki ................... 422/128 |
| 6,027,009 A | * | 2/2000 | Shinchi .................... 228/111.5 |
| 6,071,480 A | | 6/2000 | Halaka ........................ 422/128 |
| 6,152,383 A | | 11/2000 | Chen ........................ 239/102.2 |
| 6,277,332 B1 | | 8/2001 | Sucholeiki ................... 422/128 |
| 6,578,659 B1 | * | 6/2003 | Manna et al. ............... 181/142 |
| 2003/0203491 A1 | * | 10/2003 | Andrevski et al. ............ 436/46 |

FOREIGN PATENT DOCUMENTS

| | | | | |
|---|---|---|---|---|
| EP | 943405 A2 | * | 9/1999 |
| EP | 1101577 A1 | * | 5/2001 |
| JP | 62282914 A | * | 12/1987 |
| JP | 09222424 A | * | 8/1997 |

OTHER PUBLICATIONS

"One-Step Microplate Sonication: Misonix 431-T Tray Horn"; The Scientist 13[12]:14, Jun. 7, 1999.*
"96 Probe Horn"; Misonix Incorporated, web page, 2002; http://www.misonix.com/Products/index.cfm?fuseaction=viewproduct&prod=79&div=11&cat=21.*

* cited by examiner

*Primary Examiner*—Edgardo San Martin
(74) *Attorney, Agent, or Firm*—R. Neil Sudol; Henry D. Coleman; William J. Sapone

(57) ABSTRACT

An ultrasonic horn in accordance with the present invention comprises a horn body having a longitudinal transmission axis, a proximal end attachable at least indirectly to a source of ultrasonic vibrations, and a distal end with an active end face. The end face is provided with a plurality of fingers projecting parallel to one another and to the axis.

20 Claims, 2 Drawing Sheets

ULTRASONIC HORN

BACKGROUND OF THE INVENTION

This invention relates to ultrasonic vibration probes. More particularly, this invention relates to such an ultrasonic probe or horn that is particularly useful in the simultaneous sonication of biological and cellular materials disposed in multiple wells of a tray.

It has been well known for decades that a probe that vibrates at ultrasonic frequencies (i.e. frequencies greater than 16,000 Hz) and has its distal end submerged under fluids will create cavitation bubbles if the amplitude of vibration is above a certain threshold. Many devices have been commercialized which take advantage of this phenomenon. An example of such an ultrasonic cellular disrupter is disclosed in the Sonicator™ sales catalog of Misonix Incorporated of Farmingdale, N.Y. In general, devices of this type include an electronic generator for producing electrical signals with frequencies ranging from 16 to approximately 100 KHz, a piezoelectric or magnetostrictive transducer to convert the signal to mechanical vibrations and a probe (a.k.a. horn or velocity transformer) which amplifies the motion of the transducer to usable levels and projects or removes the operating face away from the transducer itself. The design and implementation of these components are well known to the art.

The cavitation bubbles produced by such ultrasonic vibration devices can be utilized to effect changes in the fluid or upon particles suspended therein. Such changes include biological cell disruption, deagglomeration of clumped particles, emulsification of immiscible liquids and removal of entrained or dissolved gases, among many others.

Cell disruption has been a particularly good application for probe type devices, in that the cells may be disrupted without the heat or cellular changes which prevent further analysis by conventional methodology. Many scientific protocols have been written which name the Sonicator™ (or similar devices) as the instrument of choice for the procedure.

In one device for ultrasonically processing multiple small samples, the Cup Horn™ manufactured by Misonix, Inc., of Farmingdale, N.Y., a probe tip is separated from the sample by a membrane or other solid surface. If liquid is present on both sides of the membrane or surface, the acoustic waves will propagate through the membrane and transfer the cavitation forces to the second liquid volume. This membrane does not have to be elastic. In fact, experience shows that glass or hard plastic is an acceptable material. Consequently, glass and plastic test tubes and beakers are routinely used in this service.

These Cup Horn devices are used primarily where the biological cells or molecules are easy to disrupt, such as liver or brain cells. With more tougher cells such as heart muscle or *e-coli* cells, the Cup Horns typically do not induce sufficient acoustic power into the tray wells since the energy must pass through the coupling fluid and membrane of the tray itself. It is therefore desired to come up with a device which induces sufficient acoustic energy into each of the wells of the tray horn simultaneously, reducing the time to treat the entire sample.

Some embodiments have been proposed or have been offered for sale for this purpose. In these embodiments, a half wave coupling block has been fashioned to which several daughter probes have been attached, with the center location of each coinciding with the center to center dimension of the tray wells. These devices have typically been very unwieldy in that their length is generally that of a full wavelength of the speed of sound in titanium. For a 20 kc system this is approximately 11 inches. Add the length of the transducer to it and an overall length of 18 inches or more is obtained.

In addition, these devices could only treat up to about 10 wells at most simultaneously, with most being significantly less than that. When greater numbers of probes were added, the uniformity of vibration suffered, in that one probe would be vibrating at a higher amplitude than the next, causing uneven yields within the wells themselves. In addition, the efficiency of vibration of these devices was low, thereby inducing thermal heating of the samples by the insertion of the hot probe.

Therefore, it is desired to obtain a device which can treat all 96 wells at one time with an invasive probe to provide sufficient acoustic energy in every well to break up the hardest biological cells, while providing equal amplitude per invasive probe all at less than a full wavelength of frequency, excluding the transducer itself.

OBJECTS OF THE INVENTION

An object of the present invention is to provide an ultrasonic device that could treat a full microtiter tray simultaneously.

Another object of the present invention is to provide such an ultrasonic device that maintains an acceptable degree of uniformity of acoustic intensity across the cells of the microtiter tray.

A further object of the present invention is to provide such an ultrasonic device which does not heat the fluid or the sample liquids, and which requires minimum energy to operate, thereby allowing the use of the device on existing laboratory scale ultrasonic processors.

These and other objects of the present invention will be apparent from the drawings and descriptions herein.

SUMMARY OF THE INVENTION

An ultrasonic horn in accordance with the present invention comprises a horn body having a longitudinal transmission axis, a proximal end attachable at least indirectly to a source of ultrasonic vibrations, and a distal end with an active end face. The end face is provided with a plurality of fingers projecting parallel to one another and to the axis.

Pursuant to another feature of the present invention, the fingers are disposed in a regular array, preferably but not necessarily a rectangular array. Also, the fingers preferably have a common length.

Pursuant to further features of the present invention, the active end face is disposed in a plane oriented substantially perpendicularly to the axis, and the horn body is prismatic. The horn body preferably has a pair of first opposing faces oriented parallel to the axis and a pair of second opposing faces oriented parallel to the axis and perpendicularly to the first opposing faces. In accordance with more particular features of the invention, the horn body is provided with a first through slot extending between the first opposing faces and two second through slots extending between the second opposing faces. The first through slot intersects the second through slots.

An ultrasonic probe or horn in accordance with the present invention comprises a prismatic block provided along one face with a plurality of projections extending substantially perpendicularly to that face. As discussed above, the projections are disposed in a regular array, preferably a rectangular array, and exhibit a common length.

A method for the processing of multiple samples of material comprises providing a plurality of fluid specimens in respective wells or containers disposed in a predetermined planar array, providing an ultrasonic horn having an active end face with a plurality of fingers or projections, and moving the horn and the wells or containers relative to one another to insert the fingers or projections into respective ones of the wells or containers so that the inserted fingers or projections are in contact with the specimens in the respective ones of the wells or containers. Thereafter, the horn is vibrated at an ultrasonic resonance frequency, while maintaining the fingers or projections in contact with the specimens in the respective ones of the wells of containers.

An ultrasonic horn or probe in accordance with the present invention is an effective apparatus to acoustically treat or disrupt biological samples within a multiwell microtiter tray.

DETAILED DESCRIPTION OF THE PREFERRED EMBODIMENTS

Figure 1:
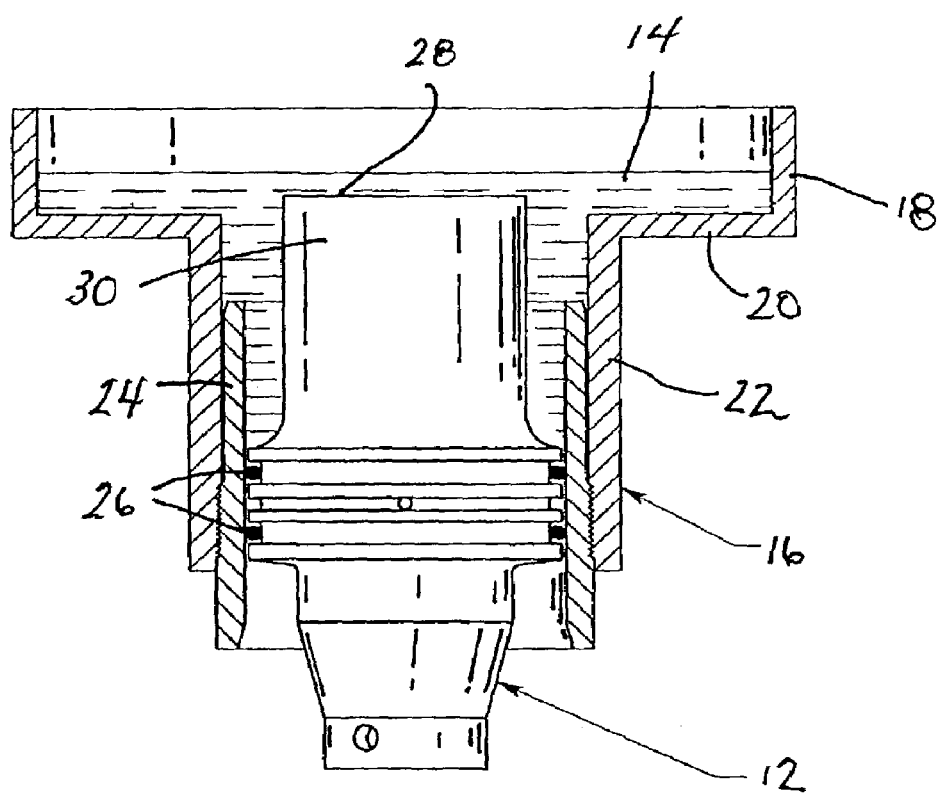
FIG. 1 is a cross-sectional view, taken along an axial plane, of an ultrasonic sonication device in accordance with the prior art.
Figure 2:
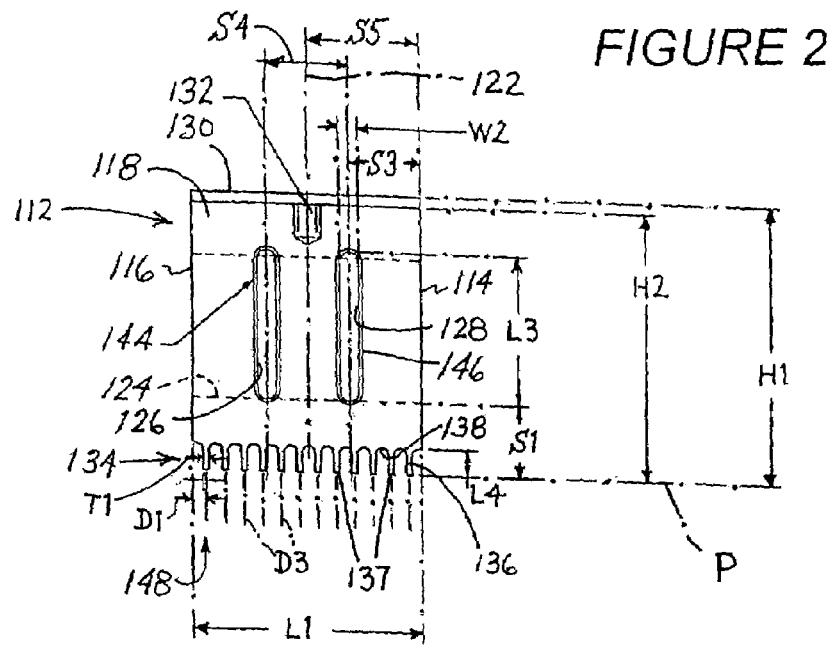
FIG. 2 is a front elevational view of an ultrasonic horn or probe in accordance with the present invention.
Figure 3:
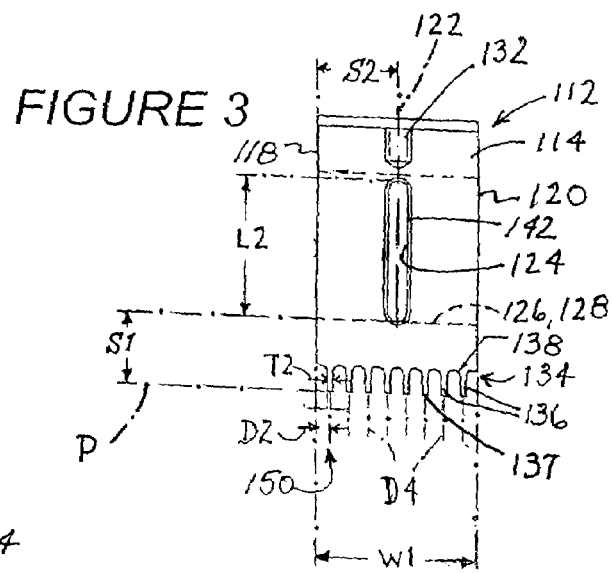
FIG. 3 is a side elevational view of the ultrasonic horn or probe of FIG. 2.
Figure 4:
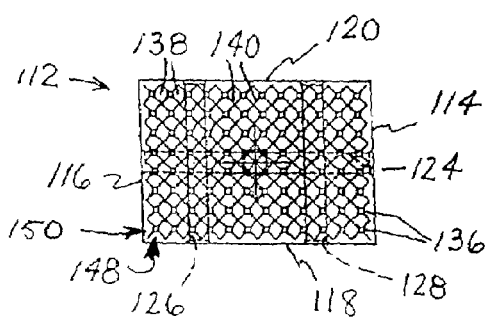
FIG. 4 is a bottom plan view of the ultrasonic horn or probe of FIGS. 2 and 3.

As illustrated in FIGS. 2–4, an ultrasonic probe or horn for use in simultaneously sonicating multiple specimens in a multi-well microtiter plate or tray (not shown) comprises a prismatic body or block 112 of substantially rigid material such as aluminum or titanium. Block 112 has a first pair of opposing lateral faces 114 and 116 and a second pair of opposing lateral faces 118 and 120, all oriented parallel to an axis of symmetry or sonication axis 122 along which longitudinal compression waves of a predetermined ultrasonic resonance frequency are conducted. Block 112 is formed with three slots 124, 126, and 128 all oriented parallel to axis 122. Slot 124 extends from one lateral face 114 to the opposite face 116, while slots 126 and 128 extend from face 118 to face 120, perpendicular to slot 124.

Horn body or block 112 is formed at a proximal end face 130 with an axially extending stud hole 132 and at a distal end face 134 with a multiplicity of equal-length fingers 136 projecting parallel to axis 122. Fingers or projections 136 are disposed in a rectangular array or grid of predetermined inter-finger distances matching the spacing between the test tubes, vials or wells of a microtiter plate or tray. As shown in FIGS. 2 and 3, fingers or projections 136 have blunt tips (not separately designated) formed at their free ends with transversely oriented flat end faces or surfaces 137. End faces 137 are disposed in a plane P oriented perpendicularly to the direction of wave transmission along horn body or block 112 and fingers or projections 136, i.e. perpendicular to sonication axis 122.

Fingers 136 are formed by drilling into block 112 perpendicularly to distal end face 134. Thus, fingers or projections 136 are integrally formed parts of horn body or block 112 and are unitary therewith. At their bases, most of the fingers 136 are surrounded by spherical sections 138 intersecting one another along groins or arched curves 140.

Slots 124, 126, and 128 may be chamfered, as indicated at 142, 144, and 146.

EXAMPLE

In a particular implementation of the ultrasonic horn or probe illustrated in FIGS. 2–4, block 112 is made of aluminum 7075-T6 and has a pretuned height H1 of 5.20 inches and an approximate tuned height H2 of 4.993 inches. The horn is tuned to a frequency of 20 KHz. Block 112 has a width W1 of 3.000 inches and a length L1 of 4.400 inches.

Slot 124 has a length L2 of 2.625 inches, while slots 126 and 128 have a length L3 of 2.750 inches. The slots have the same spacing S1 of 1.368 inches from the free ends or tips (not separately designated) of fingers 136. Slots 124, 126, 128 have a width W2 of 0.375 inch. Slot 124 has a spacing S2 of 1.500 inches from lateral faces 118 and 120. Slots 126 and 128 have a spacing S3 of 1.405 inches from lateral faces 116 and 114, respectively. Slots 126 and 128 have a mutual center-line spacing S4 of 1.590 inches.

Chamfers 142, 144, and 146 are at a 45° angle and have a thickness (not labeled) of 0.04 inch. Stud hole 132 is spaced 1.50 inches from faces 118 and 120 and has a spacing S5 of 2.200 inches from faces 114 and 116.

Fingers 136 have a length L4 of 0.500 inch, thickness dimensions T1 and T2 of 0.204±0.001 inch. A first column 148 (FIGS. 2 and 4) of fingers 136 is spaced a distance D1 of 0.251 inch from face 116, while a first row 150 (FIGS. 3 and 4) of fingers 136 is spaced a distance D2 of 0.260 inch from face 118. The remaining columns (not separately labeled) of fingers 136 are respectively spaced from the first column 148 by distances D3 of 0.354 inch, 0.709 inch, 1.063 inch, 1.417 inch, 1.772 inch, 2.126 inch, 2.480 inch, 2.835 inch, 3.189 inch, 3.543 inch, and 3.898 inch. The remaining rows (not separately designated) are respectively spaced from the first row 150 by distances D4 of 0.354 inch, 0.709 inch, 1.063 inch, 1.417 inch, 1.772 inch, 2.216 inch, and 2.480 inch. Spherical sections 138 have a radius (not indicated) of 0.125 inch.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An ultrasonic horn comprising a horn body having a longitudinal transmission axis, a proximal end attachable at least indirectly to a source of ultrasonic vibrations, and a distal end with an active end face, said end face being provided with a plurality of fingers projecting parallel to one another and to said axis, said fingers being unitary or integral with said horn body, said fingers being formed with flat end faces oriented transversely to said transmission axis, said fingers being disposed in a rectangular array.

2. The ultrasonic horn defined in claim 1 wherein said fingers have a common length.

3. The ultrasonic horn defined in claim 2 wherein said active end face is disposed in a plane oriented substantially perpendicularly to said axis.

4. The ultrasonic horn defined in claim 3 wherein said horn body is prismatic.

5. The ultrasonic horn defined in claim 4 wherein said horn body has a pair of first opposing faces oriented parallel to said axis and a pair of second opposing faces oriented parallel to said axis and perpendicularly to said first opposing faces, said horn body being provided with a through slot extending between said first opposing faces.

6. The ultrasonic horn defined in claim 5 wherein said through slot is a first through slot, said horn body being provided with a pair of second through slots extending between said second opposing faces, said first through slot intersecting said second through slots.

7. The ultrasonic horn defined in claim 1 wherein said horn body is prismatic.

8. The ultrasonic horn defined in claim 7 wherein said horn body has a pair of first opposing faces oriented parallel to said axis and a pair of second opposing faces oriented parallel to said axis and perpendicularly to said first opposing faces, said horn body being provided with a through slot extending between said first opposing faces.

9. The ultrasonic horn defined in claim 8 wherein said through slot is a first through slot, said horn body being provided with a pair of second through slots extending between said second opposing faces, said first through slot intersecting said second through slots.

10. The ultrasonic horn defined in claim 1 wherein said fingers have a common length.

11. The ultrasonic horn defined in claim 1 wherein said active face is disposed in a plane oriented substantially perpendicularly to said axis.

12. An ultrasonic probe or horn comprising a prismatic block provided along one face with a plurality of projections extending substantially perpendicularly to said face, said projections being integrally formed parts of said block and unitary therewith, said projections having tips formed as transversely oriented flat surfaces, said projections being disposed in a rectangular array.

13. The ultrasonic horn defined in claim 12 wherein said projections have a common length.

14. The ultrasonic horn defined in claim 13 wherein said face is disposed in a plane oriented substantially perpendicularly to an axis of symmetry of said block.

15. The ultrasonic horn defined in claim 14 wherein said block has a pair of first opposing faces oriented parallel to said axis and a pair of second opposing faces oriented parallel to said axis and perpendicularly to said first opposing faces, said block being provided with a through slot extending between said first opposing faces.

16. The ultrasonic horn defined in claim 15 wherein said through slot is a first through slot, said block being provided with a pair of second through slots extending between said second opposing faces, said first through slot intersecting said second through slots.

17. The ultrasonic horn defined in claim 12 wherein said block has a pair of first opposing faces oriented parallel to said axis and a pair of second opposing faces oriented parallel to said axis and perpendicularly to said first opposing faces, said block being provided with a through slot extending between said first opposing faces.

18. The ultrasonic horn defined in claim 17 wherein said through slot is a first through slot, said block being provided with a pair of second through slots extending between said second opposing faces, said first through slot intersecting said second through slots.

19. The ultrasonic horn defined in claim 12 wherein said projections have a common length.

20. An ultrasonic horn comprising a horn body having a longitudinal transmission axis, a proximal end attachable at least indirectly to a source of ultrasonic vibrations, and a distal end with an active end face, said end face being provided with a plurality of fingers projecting parallel to one another and to said axis, said fingers having base ends and fee tips, a plurality of said fingers being surrounded at respective base ends by spherical sections of said horn body intersecting one another along groins or arched curves.

* * * * *